(12) United States Patent
Karavirta

(10) Patent No.: US 10,709,382 B2
(45) Date of Patent: Jul. 14, 2020

(54) COMPUTING USER'S PHYSIOLOGICAL STATE RELATED TO PHYSICAL EXERCISES

(71) Applicant: Polar Electro Oy, Kempele (FI)

(72) Inventor: Laura Karavirta, Jyvaskyla (FI)

(73) Assignee: Polar Electro Oy, Kempele (FI)

( * ) Notice: Subject to any disclaimer, the term of this patent is extended or adjusted under 35 U.S.C. 154(b) by 797 days.

(21) Appl. No.: 14/769,862

(22) PCT Filed: Mar. 4, 2013

(86) PCT No.: PCT/EP2013/054261
§ 371 (c)(1),
(2) Date: Aug. 24, 2015

(87) PCT Pub. No.: WO2014/135187
PCT Pub. Date: Sep. 12, 2014

(65) Prior Publication Data
US 2016/0000373 A1 Jan. 7, 2016
US 2016/0235363 A9 Aug. 18, 2016

(51) Int. Cl.
*A61B 5/00* (2006.01)
*G06F 19/00* (2018.01)
*A61B 5/024* (2006.01)
*A61B 5/11* (2006.01)
*G01P 15/00* (2006.01)

(52) U.S. Cl.
CPC ........ *A61B 5/6801* (2013.01); *A61B 5/02405* (2013.01); *A61B 5/112* (2013.01); *G01P 15/00* (2013.01); *G06F 19/3481* (2013.01); *A61B 5/024* (2013.01); *A61B 5/6823* (2013.01); *A61B 5/6824* (2013.01); *A61B 5/6829* (2013.01); *A61B 2503/10* (2013.01)

(58) Field of Classification Search
CPC .......... A61B 5/1118; A61B 2562/0219; A61B 5/112; A61B 5/7275; A61B 2503/10; A61B 5/6807; A61B 5/11; A61B 5/1117
USPC ............ 600/300, 587, 595; 702/19; 434/258
See application file for complete search history.

(56) References Cited

U.S. PATENT DOCUMENTS 7,648,441 B2 * 1/2010 Silk ...................... A61B 5/1038
                                                            482/1
7,771,371 B2 * 8/2010 Avni ...................... G01L 5/008
                                                            600/592

(Continued)

FOREIGN PATENT DOCUMENTS

CN    1968293 A      5/2007
EP    2484281 A1     8/2012

(Continued)

OTHER PUBLICATIONS

International Search Report for corresponding PCT Application No. PCT/EP2013/054261, pp. 1-3 (dated Dec. 6, 2013).

(Continued)

*Primary Examiner* — May A Abouelela
(74) *Attorney, Agent, or Firm* — FisherBroyles, LLP

(57) ABSTRACT

A method, apparatus, and computer program for estimating user's physiological state from gait measurements carried out during a physical exercise are disclosed. The physiological state is computed from at least one of step interval variability and stride interval variability acquired from the gait measurements.

20 Claims, 6 Drawing Sheets

(56) References Cited

U.S. PATENT DOCUMENTS

| | | | | |
|---|---|---|---|---|
| 8,011,229 B2* | 9/2011 | Lieberman | ............ | A61B 5/1036 73/65.01 |
| 8,608,671 B2* | 12/2013 | Kinoshita | ............... | A61B 5/112 600/595 |
| 8,821,417 B2* | 9/2014 | McGregor | ............ | A61B 5/1118 600/587 |
| 9,582,072 B2* | 2/2017 | Connor | ................... | G06F 3/011 |
| 2006/0079800 A1* | 4/2006 | Martikka | ............ | A61B 5/0488 600/546 |
| 2007/0118043 A1* | 5/2007 | Oliver | .................. | A61B 5/0245 600/519 |
| 2008/0045804 A1* | 2/2008 | Williams | ............... | A61B 5/112 600/300 |
| 2008/0108913 A1* | 5/2008 | Lengsfeld | ............ | A61B 5/1038 600/595 |
| 2008/0214360 A1* | 9/2008 | Stirling | ............... | A61B 5/1038 482/9 |
| 2009/0047645 A1* | 2/2009 | Dibenedetto | .......... | G16H 15/00 434/258 |
| 2009/0240171 A1* | 9/2009 | Morris Bamberg | ........................ | A61B 5/1038 600/595 |
| 2009/0318779 A1* | 12/2009 | Tran | ..................... | A61B 5/0022 600/301 |
| 2010/0130298 A1* | 5/2010 | Dugan | ............... | A63B 69/3623 473/223 |
| 2010/0210975 A1* | 8/2010 | Anthony, III | ........ | A61B 5/0002 600/595 |
| 2010/0228154 A1* | 9/2010 | Leuthardt | ............ | A61B 5/0002 600/587 |
| 2011/0054359 A1* | 3/2011 | Sazonov | ............. | A43B 3/0005 600/595 |
| 2011/0152695 A1* | 6/2011 | Granqvist | ............ | A61B 5/0006 600/481 |
| 2011/0213278 A1* | 9/2011 | Horak | .................... | A61B 5/112 600/595 |
| 2011/0230791 A1* | 9/2011 | Ten Kate | ........... | G08B 21/0446 600/595 |
| 2011/0304497 A1* | 12/2011 | Molyneux | ............ | A43B 1/0054 342/42 |
| 2012/0071733 A1* | 3/2012 | Grey | ................... | G06F 19/3481 600/301 |
| 2012/0095356 A1* | 4/2012 | Oleson | ............... | A63B 24/0062 600/508 |
| 2012/0253234 A1* | 10/2012 | Yang | .................... | A61B 5/1038 600/595 |
| 2012/0316455 A1* | 12/2012 | Rahman | ............... | G01C 22/006 600/547 |
| 2012/0316456 A1* | 12/2012 | Rahman | .................. | G06F 1/163 600/547 |
| 2013/0041617 A1* | 2/2013 | Pease | ................... | A43B 3/0005 702/139 |
| 2013/0110011 A1* | 5/2013 | McGregor | ............ | A61B 5/1118 600/595 |
| 2013/0123669 A1* | 5/2013 | Kinoshita | .............. | A61B 5/112 600/595 |
| 2013/0131555 A1* | 5/2013 | Hook | ..................... | A61B 5/112 600/595 |
| 2013/0151193 A1* | 6/2013 | Kulach | ................... | G01P 15/02 702/141 |
| 2013/0190903 A1* | 7/2013 | Balakrishnan | ....... | A61B 5/7246 700/91 |
| 2014/0180171 A1* | 6/2014 | Hyde | ..................... | A61B 5/002 600/595 |
| 2014/0277633 A1* | 9/2014 | Flaction | .................. | G01S 19/19 700/91 |

FOREIGN PATENT DOCUMENTS

| | | |
|---|---|---|
| WO | WO2006119186 A2 | 11/2006 |
| WO | 2012007855 A1 | 1/2012 |
| WO | WO2012014714 A1 | 2/2012 |
| WO | WO2012171967 A2 | 12/2012 |

OTHER PUBLICATIONS

Chinese Search Report for corresponding Application No. 201380074240X, 2 pages, dated Dec. 19, 2017.

Notification of Second Office Action for corresponding Application No. 201380074240X, 13 pages, dated Dec. 28, 2017.

Office Action issued by the European Patent Office for corresponding EP Patent Application No. 13707173.4 dated Mar. 18, 2019, 5 pgs.

* cited by examiner

COMPUTING USER'S PHYSIOLOGICAL STATE RELATED TO PHYSICAL EXERCISES

CROSS-REFERENCE TO RELATED APPLICATION

This application is a National Stage application of International Application No. PCT/EP2013/054261, filed Mar. 4, 2013, which is incorporated by reference herein in its entirety.

BACKGROUND

1. Field

The invention relates to the field of physical exercises and training computers and, particularly, a method and a corresponding system or apparatus for computing a user's physiological state.

2. Description of the Related Art

Strenuous exercise training with inadequate recovery may induce excessive fatigue and lead to overreaching and, in the long run, to an overtraining syndrome. Overreaching and the overtraining syndrome result in impaired performance despite of strenuous and systematic training. Recreational and competitive endurance runners often have large training volumes, and they need a reliable and simple marker for early detection of excessive fatigue and associated overreaching in training. The overreaching and the overtraining syndrome may be considered as physiological states when the training is no longer efficient but, instead, may degrade the user's performance. Due to the various symptoms of overreaching and the overtraining syndrome, there is no reliable and simple marker for early detection. In addition to a method for determining the state of overreaching or the state of the overtraining syndrome, there is a need for improved methods for determining other physiological states.

SUMMARY

The invention is defined by the independent claims.

According to an aspect, there is provided an apparatus comprising: at least one processor and at least one memory including a computer program code, wherein the at least one memory and the computer program code are configured, with the at least one processor, to cause the apparatus to: acquire gait measurement data representing measured gait of a user during a physical exercise; compute at least one of step interval variability and stride interval variability from the gait measurement data; and determine user's physiological state from said at least one of step interval variability and stride interval variability.

In an embodiment, the at least one memory and the computer program code are configured, with the at least one processor, to cause the apparatus to determine the physiological state to be inversely proportional to the step interval variability and stride interval variability such that a higher step interval variability and a higher stride interval variability is associated with a poorer physiological state.

In an embodiment, the at least one memory and the computer program code are configured, with the at least one processor, to cause the apparatus to determine the user's physiological state by determining user's fatigue in training on the basis of the at least one of step interval variability and stride interval variability.

In an embodiment, the at least one memory and the computer program code are configured, with the at least one processor, to cause the apparatus to determine the user's physiological state by making a determination on user's overtraining syndrome on the basis of the at least one of step interval variability and stride interval variability.

In an embodiment, the at least one memory and the computer program code are configured, with the at least one processor, to cause the apparatus to determine the user's physiological state by determining a running performance capability of the user. The at least one memory and the computer program code may be configured, with the at least one processor, to cause the apparatus to represent the running performance capability as a numeric value in connection with another, determined reference value.

In an embodiment, the at least one memory and the computer program code are configured, with the at least one processor, to cause the apparatus to determine the user's physiological state by comparing said at least one of step interval variability and stride interval variability with at least one predetermined threshold.

In an embodiment, the at least one memory and the computer program code are configured, with the at least one processor, to cause the apparatus to: determine standard conditions for testing the physiological state; and use in the determination of the physiological state exclusively gait measurement data measured under the determined standard conditions. The at least one memory and the computer program code may be configured, with the at least one processor, to cause the apparatus to determine the standard conditions by instructing the user to provide for the determined standard conditions. The at least one memory and the computer program code may be configured, with the at least one processor, to cause the apparatus to determine the standard conditions by detecting the presence of the standard conditions during the physical exercise and acquiring the gait measurement data within a time interval during which the standard conditions are met. The at least one memory and the computer program code are configured, with the at least one processor, to cause the apparatus to test the physiological state as a background process, wherein the testing is started in the apparatus without reception of a user input. The at least one memory and the computer program code are configured, with the at least one processor, to cause the apparatus to determine the standard conditions by: detecting, after the physical exercise, the presence of the standard conditions from measurement data acquired during the physical exercise; extracting from the gait measurement data acquired during the physical exercise measurement data measured when the standard conditions are met; and determining the physiological state from the extracted measurement data as a post-processing after the physical exercise.

The at least one memory and the computer program code may be configured, with the at least one processor, to cause the apparatus to use heart activity data measured during the physical exercise as a reference for determining the presence of the standard conditions.

The at least one memory and the computer program code may be configured, with the at least one processor, to cause the apparatus to use at least one of step interval variability and stride interval variability measured during the physical exercise as a reference for determining the presence of the standard conditions.

The at least one memory and the computer program code are configured, with the at least one processor, to cause the apparatus to: determine a difference between the standard conditions and conditions prevailing during the exercise;

determine a scaling factor for the gait measurement data; and scale the gait measurement data with the scaling factor to provide the standard conditions. The at least one memory and the computer program code may be configured, with the at least one processor, to cause the apparatus to determine the scaling factor from at least one of the following measurement data acquired during the physical exercise: running speed, cadence, heart rate, heart rate variability, stride length, step length, stride interval, and step interval.

Further embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
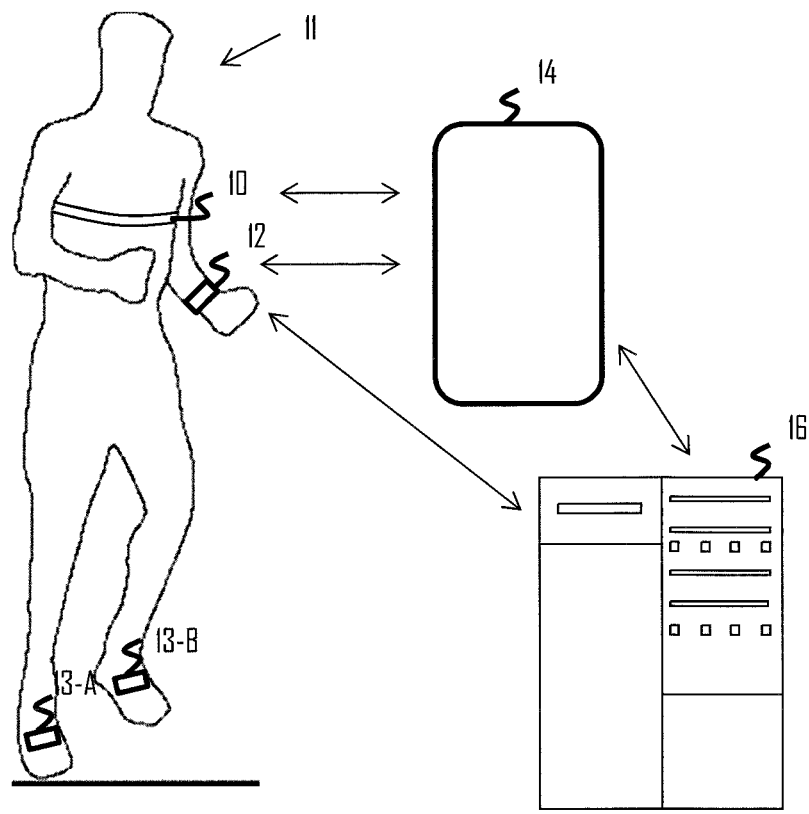
FIG. 1 illustrates a training computer system to which embodiments of the invention may be applied.

FIG. 1 illustrates an embodiment of a personal training system comprising at least one sensor device 10, 13-A, 13-B configured to measure various measurement data from a user's 11 activity during a physical exercise. The sensor devices may comprise a heart activity sensor 10 configured to measure heart activity signals from a user's 11 body. The heart activity sensor 10 may comprise one or a plurality of skin electrodes coupled to the user's 11 skin The heart activity sensor 10 may be based on detection of an electrocardiogram (ECG) signal from the user's 11 skin or optical detection of heart pulses. The heart activity sensor 10 may be provided in a strap designed to be attached around the user's chest. The strap may also comprise other sensors, e.g. at least one motion sensor based on accelerometer technology, for example.

The sensor devices may comprise at least one motion sensor 13-A, 13-B configured to monitor the user's motion during the physical exercise. In an embodiment, the at least one motion sensor 13-A, 13-B is configured to measure the user's 11 gait during the physical exercise. The at least one motion sensor 13-A, 13-B may comprise at least one stride sensor 13-A, 13-B designed to be attached to the user's 11 shoe or foot and measure the motion of the foot during the physical exercise. In another embodiment, the at least one motion sensor may comprise at least one stride sensor designed to be attached to the user's 11 torso and measure the gait from the torso. In another embodiment, the at least one motion sensor may comprise at least one stride sensor designed to be attached to the user's 11 arm and measure the gait from the arm movement. In general, the motion sensor may be designed to be located anywhere as long as it is suitable for measuring the user's 11 gait during the physical exercise.

With respect to the definition of the gait, gait is to be interpreted to comprise stepping and/or striding. Step refers to an action of two feet, while stride refers to actions of a single foot. For example, a step length is approximately half of a stride length because the user takes two steps within the same time interval as one stride. Steps may be detected by attaching a stride sensor to both feet of the user (sensors 13-A and 13-B) or a motion sensor to the torso. Strides may be detected by using only one stride sensor attached to one foot, torso, or arm. All of these different configurations measure the gait in the context of the present description.

The sensor devices 10, 13-A, 13-B may each further comprise a wireless communication circuitry configured to transmit measurement data as wireless signals to another device, e.g. a user interface device 12, 14. The user interface device 12, 14 may be configured to process the received heart activity measurement signals and to illustrate training processed from the heart activity measurement signals to the user 11 via a display unit, for example. The user interface device 12, 14 may be a training computer.

In an embodiment, the user interface device is a wrist device 12.

In an embodiment, the user interface device is a portable computer 14 such as a mobile phone or a tablet computer.

In an embodiment, the user interface device is a gym apparatus such as a treadmill.

The measurement data may further be transmitted to a server computer 16 connected to the Internet, for example. The server computer 16 may store the user's 11 user account and any training data related to the user 11. The training data may comprise the measurement data acquired during one or more physical exercises, training program data, physiological parameters of the user 11, contact details, etc. The user 11 may log into his/her user account via any electronic device capable of connecting to the Internet and comprising an Internet browser application or an application dedicated to the training. The server computer 16 may be a network server accessible only through a network connection or a personal computer (PC).

Embodiments of the invention may be carried out in any one of the above-described devices 10, 12, 13-A, 13-B, 14, 16.

Figure 2:
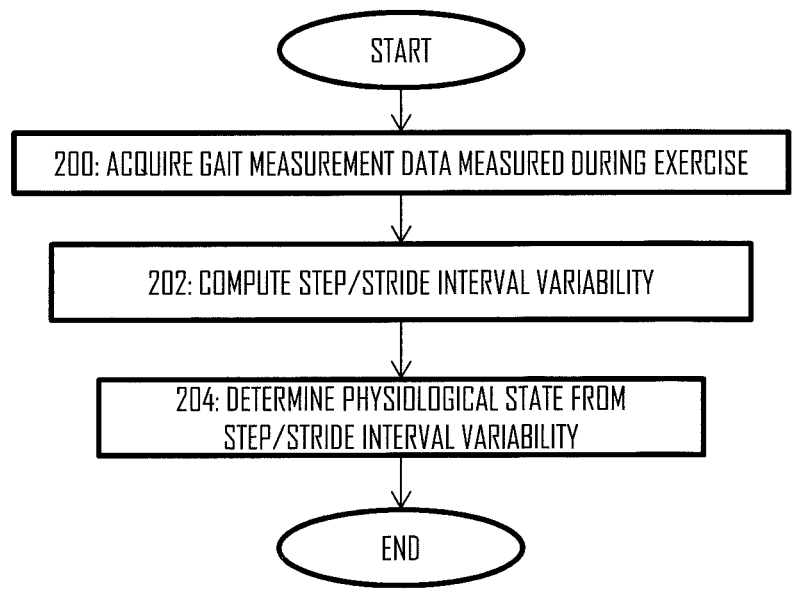
FIG. 2 is a flow diagram of a process for estimating a physiological state of a user according to an embodiment of the invention.

Let us now describe an embodiment of the invention for estimating a physiological state of the user 11 from the user's 11 gait measured during a physical exercise, e.g. a running and/or walking exercise. The physical exercise may comprise at least one training period comprising running, walking, or any other form of stepping motion where step rate is expected to remain constant over a predetermined time period, wherein the constancy is defined by predetermined limits. FIG. 2 illustrates a flow diagram of a process for estimating the physiological state of the user 11 from the user's 11 gait measured during the physical exercise. The process may be executed as a computer process in an apparatus comprising a processor and a memory storing a computer program code configuring the processor to carry out the process. According to another aspect, the process may be executed in a processing system comprising at least one processor and at least one memory storing at least one computer program code defining the process.

Referring to FIG. 2, the process comprises: acquiring gait measurement data representing measured gait of the user during a physical exercise (block 200). As described above, the gait measurements may comprise measuring the steps and/or strides of the user 11. The gait may be measured by at least one motion sensor attachable to the user 11. In block 202, at least one parameter of step interval variability and stride interval variability is computed from the gait measurement data. In block 204, the user's 11 physiological state is determined from said at least one parameter of step interval variability and stride interval variability.

The inventor has discovered that the step interval variability and stride interval variability have correlation with the user's 11 physiological state. In an embodiment, the process comprises determining from the step interval variability and/or stride interval variability whether or not the user 11 is fatigued during a training session or a training period. This may enable early detection of fatigue and, thus, prevent overreaching in training and/or the overtraining syndrome. In another embodiment, the process comprises determining from the step interval variability and/or stride interval variability whether or not the user 11 has the overtraining syndrome. In yet another embodiment, the process comprises determining the user's current state of performance as a determined metric from the step interval variability and/or stride interval variability. The state of performance may comprise running performance.

In an embodiment, the determined metric is a numeric or verbal value linked to another, determined reference value. The verbal value may comprise words defining the performance, e.g. "excellent", "good", "fair", poor".

In an embodiment, the metric comprises an estimate of the user's 11 running speed at a determined heart rate, e.g. at maximum heart rate. In this case, the numeric value is the running speed, and the reference value is the determined heart rate.

In an embodiment, the metric comprises an estimate of the user's running distance in a determined time interval, e.g. twelve (12) minutes. In this case, the numeric value is the running distance and the reference value is the determined time interval. The metric may be an estimate of time spent to travel a determined distance, e.g. a marathon. In this case, the numeric value is the time and the reference value is the distance. It should be appreciated that other metrics may be easily derived to represent the user's state of performance and/or the running performance.

Figure 3:
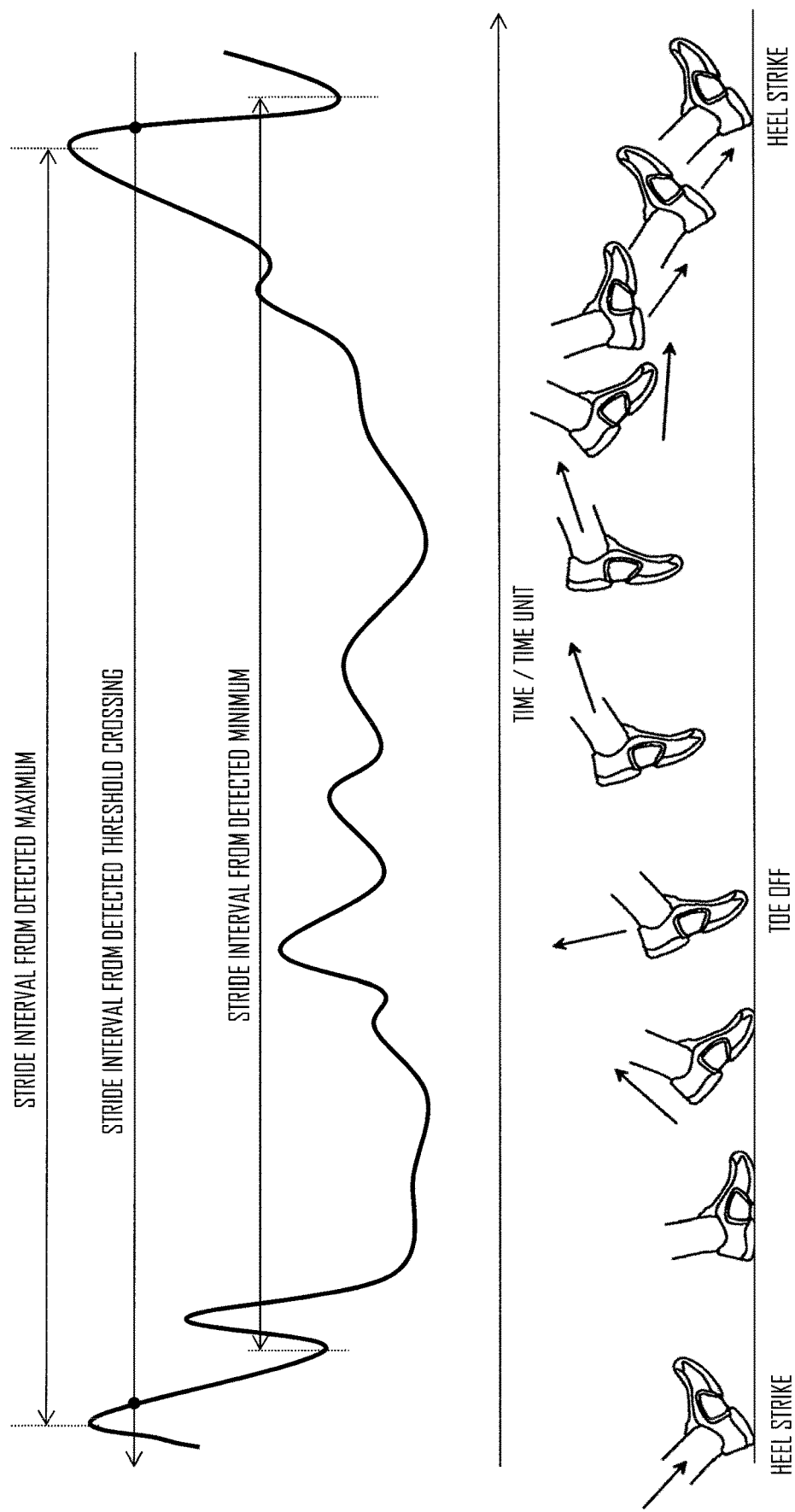
FIG. 3 illustrates gait measurement data and detection of strides according to an embodiment of the invention.

Let us now describe the gait measurements with reference to FIG. 3. In this embodiment, the gait measurement data is stride measurement data. FIG. 3 illustrates the user's 11 stride, i.e. motion of a single foot, and associated acceleration vectors at each moment of the stride. The graph illustrates measured acceleration representing the stride measurement data, wherein the acceleration may be measured by using a state-of-the-art accelerometer. The graph is illustrated as a continuous line, but it should be appreciated that the graph may be quantized, sampled and digitized into a suitable form for a digital signal processing.

Referring to FIG. 3, embodiments of the invention determining the stride interval variability may be configured to determine the stride from any periodic event in the stride measurement data. The periodic event should be understood in a broad sense, since non-zero variability in the stride intervals results in that the event used for the computation of the stride interval variability is not periodic in a strict sense. Therefore, variations in stride intervals due to digital sampling, for example, are excluded from the concept of stride interval variability. FIG. 3 illustrates some periodic events that may be detected from the stride measurement data. In an embodiment, the periodic event is an acceleration maximum resulting from the foot strike. The foot strike typically causes the highest acceleration peak and, thus, it is a periodic event that may be detected reliably by determining substantially periodic acceleration maximum values (peaks) in the stride measurement data. Another periodic event may be any other maximum value that may be detected from the stride measurement data. Yet another periodic event is a local minimum value of the stride acceleration data. In FIG. 3, the local minimum is a minimum that follows the maximum resulting from the heel strike but, equally, another local minimum may be used as the periodic event. Yet another periodic event may be a crossing point with a determined threshold level. The threshold level may be selected such that it is crossed periodically and only two times within the stride, e.g. a level which is exceeded only by the acceleration caused by the foot strike or a level below which the acceleration falls only once per stride. In order to discriminate a correct crossing point from the two crossing points between the threshold level and the stride measurement data, it may be evaluated whether the acceleration is ascending or descending when the stride measurement data crosses the threshold level. In the example of FIG. 3, the periodic event is the crossing point where the stride measurement data descends when it crosses the threshold level, and all crossing points where the stride measurement data descends when it crosses the threshold level may be selected as the periodic event for the analysis of the stride interval variability.

In the embodiments where the step interval variability is used instead of the stride interval variability, the gait measurement data may be step measurement data which may comprise two sets of stride measurement data, one for each foot. The two sets of the stride measurement data may be offset by half a stride with respect to each other due to the nature of human gait, assuming steady running. The same periodic events may be selected from the stride measurement data of different feet, e.g. maxima caused by the heel strikes.

The step/stride intervals may be computed by computing a time interval between samples representing consecutive periodic events in the step/stride measurement data. The step intervals represent a time interval between consecutive steps, while the stride intervals represent a time interval between consecutive strides. The computation of the step interval variability and the stride interval variability is substantially similar. Obviously, the step/stride interval variability refers to the degree how much step/stride intervals vary within an observation interval. The variability may be represented by deviation or variance, for example. In an embodiment, the step/stride interval variability is computed from the step/stride measurement data by computing an average value of the step/stride intervals within the observation interval and by computing a standard deviation of the step/stride intervals from the computed average. In another embodiment, differences between consecutive step/stride intervals are computed, and an average of the differences is computed to represent the step/stride interval variability. In yet another embodiment, the step/stride measurement data is transformed into a frequency domain, e.g. by applying a Fourier transform, and the transformed step/stride measurement data is subjected to spectral analysis, wherein lowfrequency components represent the step/stride interval variability. Frequency domain analysis is based on frequency decomposition of a fluctuating signal. Different frequency components can be determined in a spectrum which provides information on the distribution of the variability. The different components are often quantified in absolute values of power or in normalized units in proportion to the total power. In yet other embodiments non-linear methods such as detrended fluctuation analysis and/or entropy analysis may be used to compute the step/stride interval variability.

As described above, the step and stride interval variability correlates with the user's physiological state. According to an aspect, the step/stride interval variability increases when the user's level of fatigue or related physiological state increases and vice versa. Accordingly, the step/stride interval variability may be inversely proportional to the level of the physiological state. This physiological reaction may indicate normal tiredness and related change in stride.

In an embodiment, the step and stride variability decreases when the user's level of fatigue or related physiological state increases. In this case, a parameter characterizing fatigue and computed from the step/stride interval variability may be directly proportional to the level of the physiological state. This may indicate an overcompensation reaction in the running performance.

It should be noted that the physiological interpretation of the step and stride interval variability may depend on the long-term and short-term training history. Furthermore, the physiological interpretation may depend on the step/stride cadence and related reference value.

Figure 4:
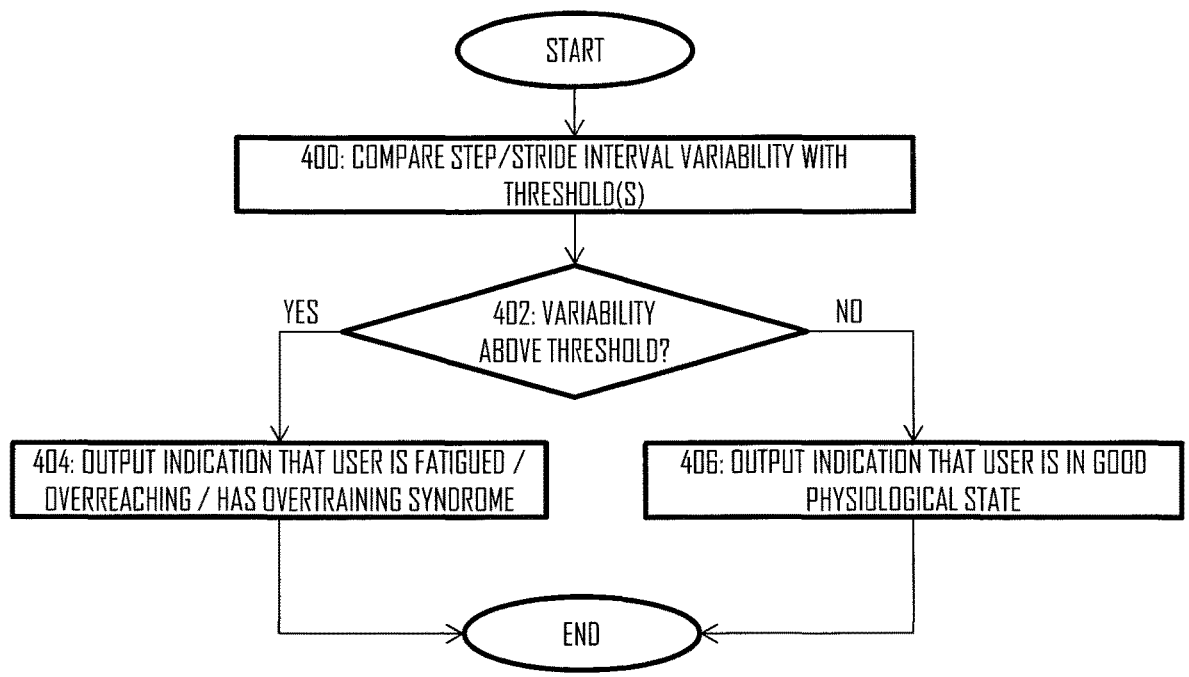
FIG. 4 is a flow diagram of a process for determining whether or not the user is overreaching or has an overtraining syndrome according to an embodiment of the invention.

In an embodiment, at least one threshold is used to determine the physiological state from the step/stride interval variability. FIG. 4 illustrates a process according to such an embodiment. Referring to FIG. 4, the step/stride interval variability is compared with at least one threshold in block 400. One threshold may be selected for determining whether or not the user is overreaching, while another threshold may be selected for determining whether or not the user has the overtraining syndrome. Yet another threshold may be selected for determining whether or not the user is too fatigued to carry out the exercise. The process may comprise comparison between prevailing values of the step/stride interval variability to the normal step/stride interval values of the user. The normal values may have been acquired as the reference values when the user is well rested and is known to be in a good physiological state. In block 402, it is determined whether or not the step/stride interval variability is above/below a threshold. Block 402 may be executed for each threshold separately. If the step/stride interval variability is determined to be above/below the threshold in block 402, the process proceeds to block 404 in which the process outputs an indication that the user is overreaching or has the overtraining syndrome, depending on the threshold used in the comparison. The degree of may vary and can be detected from the value of the step/stride variability.

The output may comprise storing the indication in a memory for later review and/or outputting the indication to the user 11 via a user interface. If the step/stride interval variability is determined to be within a normal range in block 402, the process proceeds to block 406 in which the process outputs an indication that the user is in good physiological state. The output may comprise storing the indication in a memory for later review and/or outputting the indication to the user 11 via a user interface. In the embodiments where multiple comparisons are made, the indication of the good physiological state may be output, if the step/stride interval variability is below all the thresholds that are associated with the overreaching or the overtraining syndrome.

In another embodiment, the physiological state is determined from the step/stride interval variability by mapping the computed step/stride interval variability to a table value representing the mapping between different step/stride interval variabilities and corresponding physiological states. The table values may be constructed from statistical analysis of a population. The population may comprise people with different attributes such as age, gender, weight, fitness level, etc., and their performance and associated step/stride interval variability may be recorded. The performance may relate to the running speed at a determined heart rate(s), running distance in a determined time period, or time spent to travel a determined distance, running technique at a determined speed, for example. With the prior knowledge of the user's personal attributes, the table thus provides sufficient information on the physiological state to be retrieved when the user's 11 step/stride interval variability has been measured.

Depending on the training profile of the user 11, the user may carry out physical exercises under different conditions, e.g. sometimes the user may run on flat terrain while another exercise may be an uphill running exercise. As regards the terrain factors, the slope (up/downslope) may affect the gait characteristics and may result in change of the step/stride intervals and, in particular, step/stride interval variability. Similarly, terrain roughness may affect the step/stride interval variability and distort the performance of the estimation of the physiological state.

In an embodiment, the physiological state is evaluated when the physical exercise meets standard conditions in order to make the evaluation of the physiological state comparable and effective. A standard condition may be defined as a combination of secondary factors or circumstances affecting the step or stride variability value. Such factors may characterise the user's status, the status of the current exercise, or the status of the environment, for example. The standard conditions may be selected arbitrarily provided that the same or similar standard conditions are reproducible or practically possible.

Figure 5:
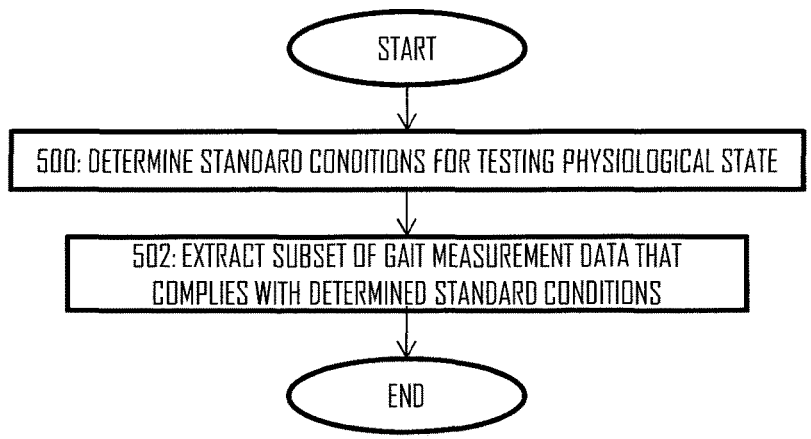
FIG. 5 is a flow diagram of a process for controlling that the physiological state is evaluated from gait measurement data acquired under standard conditions according to an embodiment of the invention.

FIG. 5 illustrates a process for ensuring that the physiological state is evaluated under the determined standard conditions. Referring to FIG. 5, the standard conditions for testing the physiological state are determined in block 500. The apparatus executing the process may store in its memory unit a database comprising the definitions for the standard conditions. Embodiments of the standard conditions are described below. Block 500 may comprise retrieving the definitions for the standard conditions from the memory and comparing conditions during the physical exercise with standard conditions in order to determine when the standard conditions are satisfied during the exercise. Upon determining that the standard conditions are met, gait measurement data is acquired while the standard conditions are considered to be satisfied (block 502). The gait measurement data meeting the standard conditions may be acquired in real time as it is being measured, or the gait measurement data meeting the standard conditions may be extracted from measured gait measurement data in post-processing after the physical exercise, for example.

In an embodiment, the standard conditions comprise a characterization of a terrain slope. The terrain slope is estimated, e.g. by using elevation change information and/or the distance information acquired, and the terrain slope is used to determine whether or not the standard conditions are met. The elevation change information may be obtained from pressure sensor, satellite-based navigation sensor, and/or from map information when the location is known. The slope information may be compared with reference slope information acquired from the database and comprising a maximum slope to still meet the standard conditions. If the estimated slope is below the maximum slope on the basis of comparison between them, the standard conditions are determined to be met. If the estimated slope is above the maximum slope on the basis of the comparison, the standard conditions are determined not to be met.

In an embodiment, the standard conditions comprise a characterization of terrain roughness or other local structure in terrain. The terrain roughness or other local structure in terrain is estimated, e.g. by comparing the measured stride interval variability or other parameter obtained from the acceleration signal with a threshold or a reference value defining the standard conditions. If the measured stride interval variability exceeds the threshold, the run is determined to have been carried out in an inappropriate terrain, and the standard conditions have not been met. If the measured stride interval variability is below the threshold, the run is determined to have been carried out in an appropriate terrain, and the standard conditions have been met.

In an embodiment, the standard conditions comprise temperature. The temperature may be measured and it may be determined whether or not the measured temperature complies with the temperature range associated with the standard conditions. If the temperature is outside the range, the standard conditions are considered not to have been met. If the temperature is within the range, the standard conditions are considered to have been met.

In an embodiment, the standard conditions comprise heart activity measurement data. The heart activity data may comprise measured heart rate or heart rate variability and is used to determine whether or not the standard conditions have been met. The heart activity measurement data may represent the user's 11 relative intensity during the exercise. The database may store at least one threshold or range for the heart activity measurement data to define the standard conditions, and the acquired heart activity measurement data may be compared with the at least one threshold or range. If the heart activity measurement data falls outside the range defining the standard conditions, the standard conditions are determined not to have been met. If the heart activity measurement data falls within the range defining the standard conditions, the standard conditions are determined to have been met.

In an embodiment, the standard conditions are defined by running speed. The running speed may be measured from the step/stride measurement data during the exercise with the prior knowledge of the step/stride length. If the running speed falls within a predetermined range defining the standard conditions, the standard conditions are deemed to be fulfilled. If the running speed falls outside the predetermined range defining the standard conditions, the standard conditions are deemed not to be fulfilled. In an embodiment, the predetermined range may comprise by a maximum threshold defining an upper limit for the running speed, and the standard conditions are met if the measured running speed is below the maximum threshold. It may be advantageous to test the physiological state when the user is not running at maximum speed in order to maintain the speed relatively constant during the testing.

In an embodiment, the standard conditions are defined by a stride interval. If measured stride interval falls within a predetermined range, the standard conditions are deemed to be fulfilled. If measured stride interval falls outside the predetermined range, the standard conditions are deemed not to be fulfilled.

In an embodiment, the standard conditions are defined by stride length. The stride length may be measured by at least one motion sensor measuring acceleration. If the measured stride length falls within a predetermined range, the standard conditions are deemed to be fulfilled. If the measured stride length falls outside the predetermined range, the standard conditions are deemed not to be fulfilled.

Figure 6:
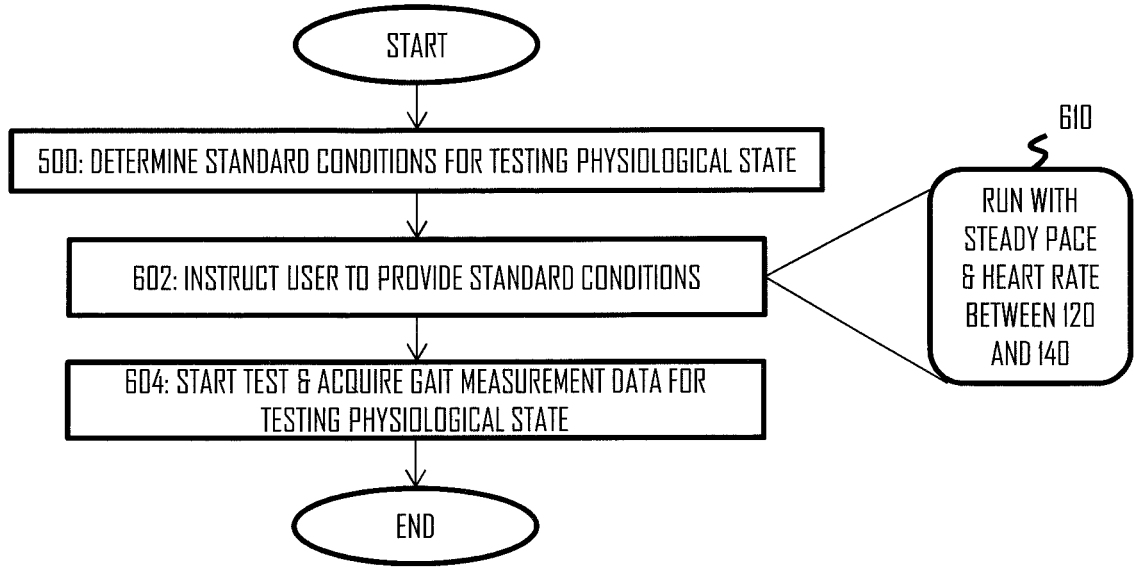
FIGS. 6 to 8 illustrate embodiments for evaluating the physiological state from the gait measurement data acquired under the standard conditions.
Figure 7:
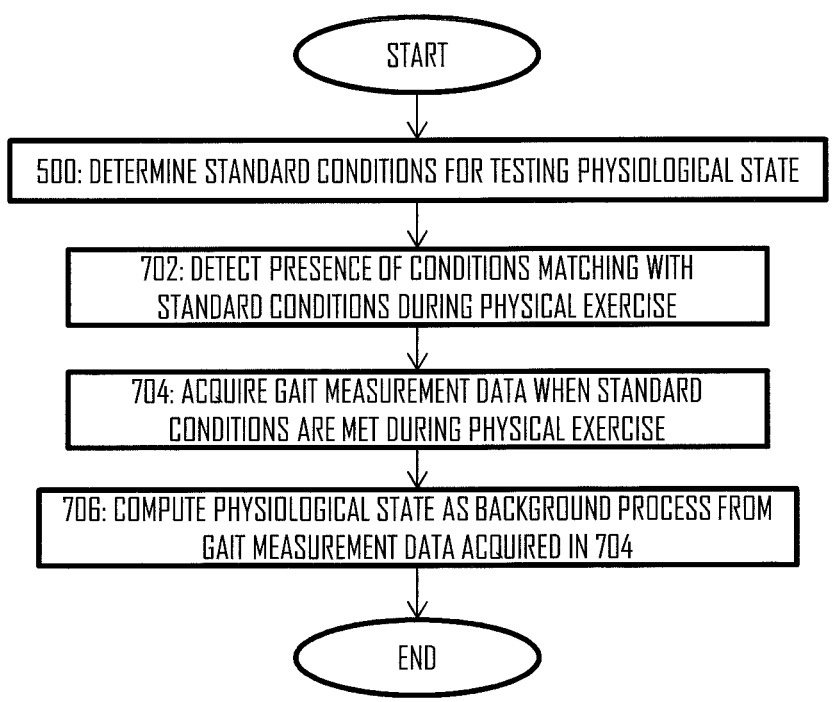
Figure 8:
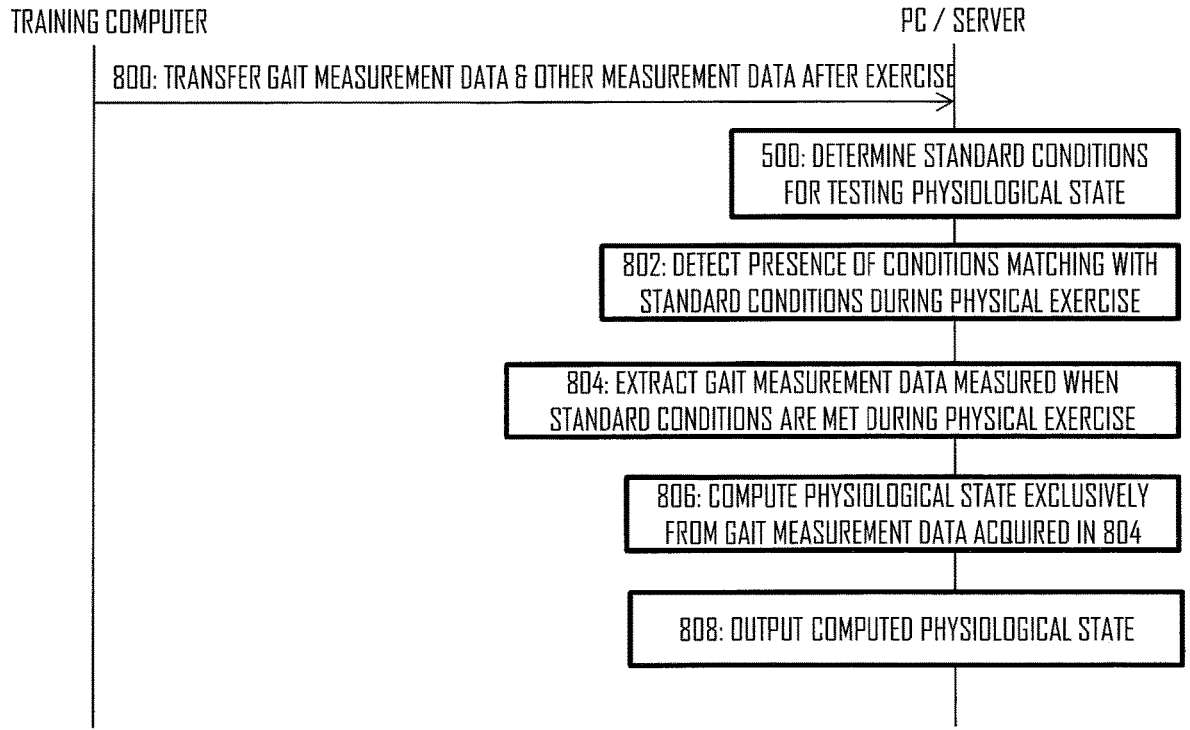

Let us now consider some embodiments for determining that the standard conditions have been met with reference to FIGS. 6 to 8. The testing of the physiological state may be carried out during the physical exercise or as a post processing after the physical exercise. In the embodiment of FIG. 6, the apparatus testing the physiological state is configured to instruct the user 11 to provide the standard conditions for testing the physiological state. The process of FIG. 6 may be triggered during the exercise, it may be triggered before the start of the physical exercise but after the user has initialized the apparatus for the exercise, e.g. by pressing "start exercise" button of the apparatus, or it may be triggered when the apparatus is in a standby state (e.g. no exercise has been started or initialized to be started). The instructions provided by the apparatus may be matched with the determined standard conditions.

Referring to FIG. 6, the apparatus retrieves the definitions for the standard conditions from the memory unit in block 500, as described above. The apparatus may alternatively or additionally retrieve instructions associated with the standard conditions from a text file, for example. In block 602, the apparatus outputs the instructions to the user via a user interface of the apparatus, e.g. a display screen 610 of the training computer 12, 14. The instructions may instruct the user to maintain a steady pace in the running and/or maintain at least some above-described parameters measured during the exercise within the range(s) complying with the standard conditions. For example, the instructions may instruct the user to maintain a determined heart rate, run at a determined speed maintain a determined stride interval or cadence, etc. After outputting the instructions, the apparatus may start acquiring the gait measurement data for testing the physiological state. In an embodiment, the apparatus may monitor that the standard conditions are met while acquiring the gait measurement data in order to ensure that the gait measurement data used for testing the physiological state comply with the standard conditions. In another embodiment, the apparatus acquires the gait measurement data for a determined time interval after providing the instructions without making the verification whether or not the standard conditions are met.

Execution of block 604 may be triggered by detecting a user input via the user interface. The user input may be understood as a confirmation that the user 11 has read the instructions and is complying with them.

In the embodiment of FIG. 6, the user 11 may be aware of the execution of the test. FIG. 7 illustrates an embodiment of a process where the physiological state may be tested as a background process without the user 11 being aware of the testing. The apparatus may start the process without reception of a user input, for example. The process of FIG. 7 may be carried out during the physical exercise, e.g. after the user has activated the apparatus to start a training mode in which the apparatus acquires and processes measurement data during the exercise. Referring to FIG. 7, the apparatus determines the standard conditions in block 500. In block 702, the apparatus monitors at least some of the measurement data measured during the exercise and compares the measurement data with the definitions of the standard conditions. As described above, the measurement data may comprise the heart activity measurement data and/or gait measurement data. Block 702 may comprise determining when the standard conditions are met during the exercise. In block 704, gait measurement data associated with those time instants when the standard conditions are met is acquired, and the gait measurement data acquired in block 704 is used in computing the physiological state in block 706. As the apparatus determines the presence of the standard conditions and computes the physiological state autonomously without interaction with the user, the process of FIG. 7 may be carried out as a background process without any user interaction. The result of the process may, however, be output to the user during the exercise and/or after the exercise. For example, if the result of the process the detection that the user is overreaching or has an overtraining syndrome, the apparatus may output the result immediately after the completion of block 706 during the exercise in order to prevent the user from further overreaching. If the result of the process is the detection that the user has a good physiological state, the result may be output only after the exercise.

FIG. 8 illustrates yet another embodiment where the physiological state is tested in the server computer 16 during and/or after the exercise on the basis of the gait measurement data transferred from the training computer 12, 14 to the server computer 16. Referring to FIG. 8, the gait measurement data and, optionally, other measurement data is transmitted from the training computer 12, 14 to the server computer 16 in step 800, and the server computer 16 receives the measurement data. Step 800 may be executed during the physical exercise such that the training computer 12, 14 streams the measurement data to the server computer 16, or it may be executed after the exercise such that the training computer 12, 14 transfers the measurement data to the server computer 16 as a bundle. A network connection through the Internet, for example, may be provided between the training computer 12, 14 and the server computer 16.

In block 500, the server computer 16 determines the standard conditions. In block 802, the server computer analyzes the received measurement data and determines time instants when the standard conditions have been met during the exercise. Block 802 may comprise comparing the gait measurement data and/or the heart activity measurement data with the one or more threshold defining the standard conditions, as described above, and determining the time instants on the basis of the comparison. As a result, the server computer 16 may determine the portions of the gait measurement data that have been measured under the standard conditions. At least a subset of the gait measurement data measured under the standard conditions is then extracted in block 804 for the evaluation of the physiological state, and the physiological state is evaluated in block 806 on the basis of the gait measurement data extracted in block 804. In an embodiment, the physiological state is evaluated exclusively on the basis of the gait measurement data extracted in block 804. Block 804 may thus be considered as a step for excluding gait measurement data that does not meet the definitions for the standard conditions.

The computed physiological state may then be output to the user 11 in block 808. In the embodiments where the process of FIG. 8 is carried out during the exercise, the server computer 16 may transmit the computed physiological state to the training computer 12, 14 during the exercise.

Figure 9:
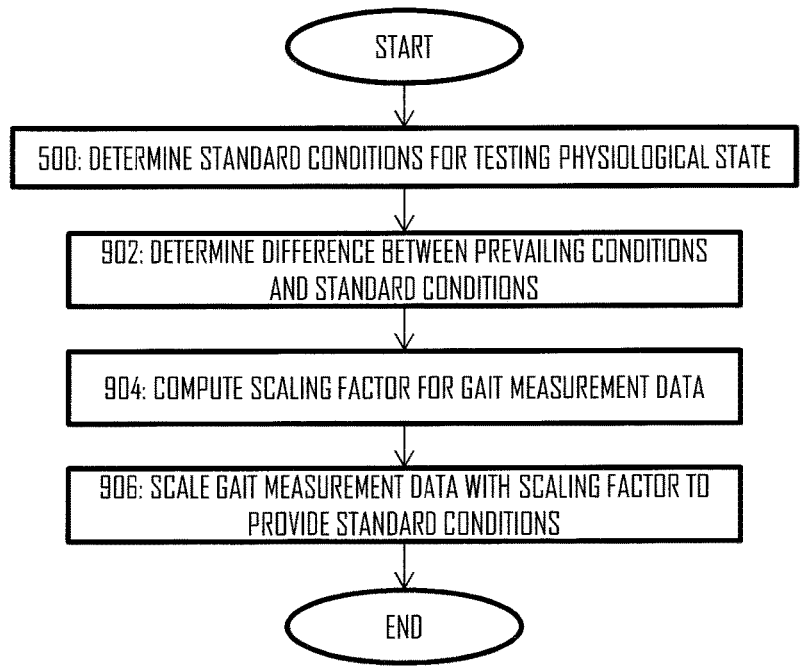
FIG. 9 illustrates a process for scaling the gait measurement data and to compute the physiological state from the scaled gait measurement data according to an embodiment of the invention.

Some embodiments of the invention evaluate the physiological state even though the standard conditions are not necessarily met. This may be achieved by scaling the gait measurement data such that it meets the standard conditions. For example, the step/stride interval variability may be proportional to the running speed. These embodiments may determine how much the current conditions (e.g. the running speed) distort the step/stride interval variability and mitigate the effect from the step/stride interval variability. FIG. 9 illustrates a process for scaling the step/stride interval variability in order to artificially provide the standard conditions.

Referring to FIG. 9, the standard conditions are determined in block 500 and, additionally, prevailing conditions may be determined. The prevailing conditions may be defined by any one of the above-described parameters measured during the exercise, e.g. the heart rate, heart rate variability, stride interval, stride length, cadence, running speed, or a reciprocal of any one of these parameters. When the heart rate maximum is known, it is possible to estimate the maximal aerobic running speed from the heart rate at a given running speed. On the basis of this knowledge, it is possible to build an association table between the heart rates and the running speeds. Accordingly, the scaling factor may be derived from the running speed, heart rate, or any related parameter.

In block 902, the difference between the prevailing conditions and the standard conditions is determined, and a scaling factor corresponding to the difference is computed in block 904. Alternatively, the scaling factor may be computed in block 904 without execution of block 902, e.g. the prevailing conditions may be mapped directly to the scaling factor by using a look-up table, for example. In block 906, the gait measurement data, the step/stride interval variability, and/or any intermediate data between the gait measurement data and the step/stride interval variability is scaled with the scaling factor. This arrangement of negating the effect of the running speed on the step/stride interval variability may enable prolonged step/stride interval variability determination during the exercise and, thus, improve the statistical significance of the determination of the physiological state by providing a greater amount of measurement data for use in the computation of the physiological state. Furthermore, this arrangement enables to compare and/or combine different step/stride interval variability tests which have been carried out at different running speeds.

In an embodiment, the step/stride interval variability decreases in proportion to the running speed and/or the heart rate. Accordingly, the scaling factor may adjust the step/stride interval variability correspondingly on the basis of the computed heart rate or the running speed. In general, the step/stride interval variability may be scaled inverse proportionally to the determined running speed and/or the heart rate.

Measures of heart rate and heart rate variability are commonly used parameters for detecting training related fatigue in different settings. Heart rate variability is an indirect marker of cardiac autonomic function whereas stride interval variability may reflect the neuromuscular function. Combining the information obtained from both heart rate variability and stride interval variability may give comprehensive data on the prevailing physiological state. In an embodiment, both step/stride interval variability and heart rate variability are used in combination to determine the physiological state. Thus, a more accurate estimate of the physiological state may be acquired by using several types of input measurement data.

In an embodiment, the standard conditions are defined by a training history in the current exercise and/or in one or more previous exercises. The training history is typically defined by an accumulating training parameter, such as elapsed time, accumulated exertion parameter, running distance, physical activity accumulation from motion sensing, etc. The accumulated exertion parameters may include energy expenditure or training load obtained from the heart rate and/or motion sensing. The standard conditions may be defined in terms of training history spanning from the start of the exercise to a determined time instant after the starting point of the exercise, wherein the determined time instant may be before the end of the exercise. The training history as the definition of the standard conditions may be used to ensure that the physiological state is estimated always under the same training conditions, e.g. after the user 11 has warmed up or at a determined stage of a training program. The parameters defining the training history as the standard conditions may comprise accumulation of the heart rate, accumulation of the strides/steps, or any parameter described above.

Figure 10:
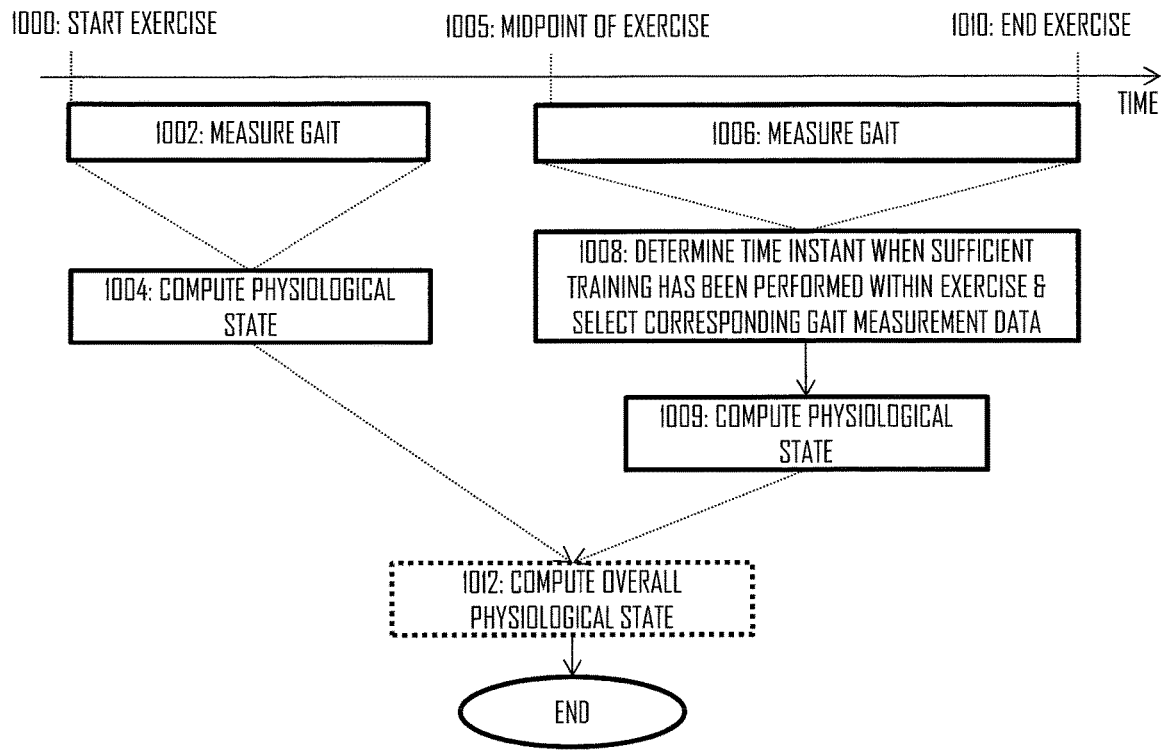
FIG. 10 illustrates a process for computing the physiological state from gait measurement data acquired at various time instants during the physical exercise according to some embodiments of the invention.

With respect to the timing of the gait measurement data acquired for the estimation of the physiological state, let us consider some embodiments for acquiring the gait measurement data from a sub-interval during the exercise and excluding at least some of gait measurement data measured outside the determined sub-interval from the estimation of the physiological state. FIG. 10 illustrates a flow diagram in connection with a time line representing the timing of the physical exercise. The exercise starts at time instant denoted by vertical line 1000, midpoint of the exercise is denoted by 1005, and the end of the exercise is denoted by 1010.

In an embodiment of the invention, the time period for the test is at the beginning of the exercise. In this case, the step/stride interval variability characterizes the user's physiological state before the exercise session. In this case, the current exercise has low impact on the test result. With respect to this embodiment, gait measurement data is acquired in block 1002 at the beginning of the exercise until a determined time instant after the beginning of the exercise. This time instant may be before the midpoint 1005. The width of block 1002 may represent for how long the gait measurement data is acquired. The physiological state is then computed in block 1004 from the gait measurement data acquired in block 1002.

In an embodiment of the invention, the time period for testing the physiological state is started once a predefined training history from the start of the exercise has expired. The training history may be represented by a determined non-zero time interval counted from the start of the exercise 1000. In this case, the step/stride interval variability characterizes the user's 11 physiological state during the exercise session. In this case, the user's 11 physiological status before the test and the impact of the current exercise both contribute to the test result. The measurements in the beginning and at the end of the current exercise may also be compared to evaluate the impact of the current exercise session. Referring to FIG. 10, the gait measurement data for this test is acquired in block 1006. This gait measurement data may be acquired mainly during the latter half of the exercise, although the acquisition may be started in the former half of the exercise. It should be appreciated that the gait measurement data may be acquired also between blocks 1002 and 1006. In block 1008, the portion of the gait measurement data acquired in block 1006 and acquired when the sufficient training history during the exercise has been achieved is selected, and the physiological state is computed from the selected gait measurement data in block 1009.

The process may additionally comprise block 1012 in which the results of blocks 1004 and 1009 are combined. The combination may comprise determining the user's 11 overall physiological state on the basis of the physiological states computed in blocks 1004 and 1009. Alternatively, the physiological states computed in blocks 1004 and 1009 may be output separately via the user interface.

Figure 11:
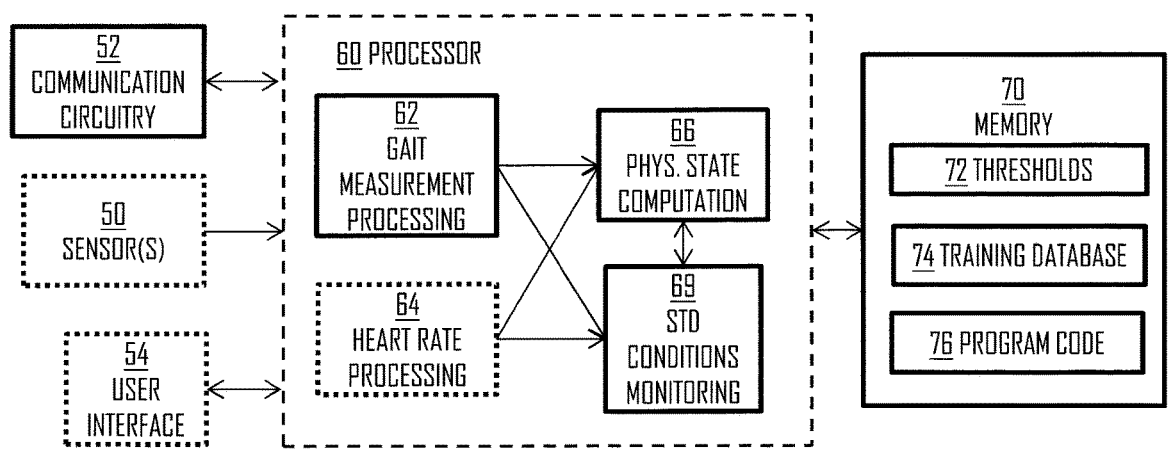
FIG. 11 is a block diagram of an apparatus according to an embodiment of the invention.

FIG. 11 illustrates a block diagram of an apparatus according to an embodiment of the invention. As described above, the apparatus may be any one of the devices 10, 12, 13-A, 13-B, 14, 16, or any other apparatus configured to process measurement signals measured from the user's body during the physical exercise. The apparatus comprises a least one processor 60 and at least one memory 70 storing a computer program code 76. The computer program code 76 configures the processor 60 to carry out embodiments of the invention, e.g. any one of the embodiments described above. The memory 70 may further store a training database 74 in which any parameters, performance metrics, and/or physiological states measured and/or computed during or after the exercise may be stored. The memory 70 may further store any thresholds 72 and/or any other parameters or criteria used in the embodiments described above, e.g. the thresholds for use in the evaluation of the physiological state and the thresholds for use in determining whether or not the standard conditions for the exercise have been met.

The apparatus may further comprise a communication circuitry 52 providing the apparatus with communication capability. The communication circuitry 52 may support any wired or wireless communication technique, e.g. Bluetooth, Bluetooth Low energy, IEEE 802.15, IEEE 802.11, W.I.N.D, ANT by Dynastream, or any other radio or induction-based communication technique. Depending on the embodiment, the apparatus may further comprise at least one sensor 50 configured to measure the heart activity of the user 11 and/or the gait of the user 11. Depending on the embodiment, the apparatus may further comprise the user interface 54 for user interaction. The user interface 54 may comprise an output device and an input device. The output device may comprise a display unit (e.g. a liquid crystal display) and the input device may comprise one or more buttons or keys or a touch-sensitive display.

The processor 60 may comprise one or more sub-circuitries 62 to 69 configured to carry out the embodiments of the invention. The sub-circuitries 62 to 69 may be physical circuitries in the processor 60, or they may be realized by separate computer program modules, and the at least partially the same physical circuitries of the processor may carry out the operations of different modules 62 to 69.

The processor 60 may receive the measurement signals from the at least one sensor 50 and/or through the communication circuitry 52. The processor may comprise a gait measurement processing circuitry 62 configured to process the gait measurement data and, optionally, a heart rate processing circuitry 64 configured to process heart activity measurement signals. The gait measurement circuitry 62 may be configured to compute the step/stride intervals and/or the step/stride interval variability from the gait measurement data. The heart rate processing circuitry 64 may be configured to compute the heart rate and/or heart rate variability from the received heart activity measurement data.

The processor 60 may further comprise a physiological state computation circuitry 66 configured to compute the physiological state from at least the data received from the gait measurement processing circuitry 62 according to any one of the above-described embodiments. In some embodiments, the physiological state computation circuitry 66 is configured to scale the step/stride interval variability with a scaling factor determined on the basis of the gait measurement data and/or the heart activity measurement data.

The processor 60 may further comprise a standard conditions monitoring circuitry 69 configured to control that the physiological state computation circuitry 66 computes the physiological state from the gait measurement data measured under the standard conditions. The standard conditions monitoring circuitry 69 may be configured to monitor at least one of the gait measurement data and the heart activity measurement data in order to determine the time instants when the standard conditions are met. The standard conditions monitoring circuitry 69 may use at least some of the thresholds 72 as a reference for the standard conditions. The standard conditions monitoring circuitry 69 may then control the physiological state computation circuitry 66 to compute the physiological state only from the gait measurement data measured under the standard conditions, as described above.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in FIGS. 2 to 10 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to training processing systems defined above but also to other suitable systems. Any development of the systems may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

The invention claimed is:

1. A method for determining a physiological state of a user by an apparatus, the method comprising:
acquiring, in the apparatus, gait measurement data from at least one motion sensor representing measured gait of the user during a physical exercise;
computing, in the apparatus, at least one of step interval variability and stride interval variability from the gait measurement data;
determining, in the apparatus standard conditions for testing a level of fatigue;
determining, by the apparatus, the user's level of fatigue from said at least one of step interval variability and stride interval variability and using, in the determination of the level of fatigue, exclusively gait measurement data measured under the standard conditions by excluding from the determination of the level of fatigue the gait measurement data that has been measured outside the standard conditions; and
determining when the standard conditions are satisfied by using the following steps (a) and (b):
(a) the standard conditions are defined by heart activity measurement data received from a heart activity sensor and at least one threshold or range for the heart activity measurement data, and the apparatus compares the measured heart activity measurement data with the at least one threshold or range; if the heart activity measurement data falls outside the range defining the standard conditions, the apparatus determines the standard conditions not to have been met; and
if the heart activity measurement data falls within the range defining the standard conditions, the apparatus determines the standard conditions to have been met;
(b) the standard conditions are defined by running speed measured from the gait measurement data during the exercise with prior knowledge of a step length or a stride length; if the measured running speed falls within a predetermined range defining the standard conditions, the apparatus determines the standard conditions to be fulfilled; and if the measured running speed falls outside the predetermined range defining the standard conditions, the apparatus determines the standard conditions not to be fulfilled.

2. The method of claim 1, wherein the physiological state is determined to be inversely proportional to the step interval variability and stride interval variability such that a higher step interval variability and a higher stride interval variability is associated with a poorer physiological state.

3. The method of claim 1, wherein said determining the user's physiological state comprises determining the user's level of fatigue in training on a basis of the at least one of step interval variability and stride interval variability.

4. The method of claim 1, wherein said determining the user's physiological state comprises making a determination on user's overtraining syndrome on a basis of the at least one of step interval variability and stride interval variability.

5. The method of claim 1, wherein said determining the user's physiological state comprises determining a running performance capability of the user.

6. The method of claim 5, further comprising representing the running performance capability as a numeric value in connection with a separate determined reference value.

7. The method of claim 1, further comprising determining, in the apparatus, the user's physiological state by comparing said at least one of step interval variability and stride interval variability with at least one predetermined threshold.

8. The method of claim 1, further comprising:
determining, in the apparatus, standard conditions for testing the physiological state; and
using, in the apparatus, in the determination of the physiological state exclusively gait measurement data measured under the determined standard conditions.

9. The method of claim 8, wherein said determining the standard conditions in the apparatus comprises instructing the user to provide input related to the determined standard conditions.

10. The method of claim 8, wherein said determining the standard conditions in the apparatus comprises detecting on a presence of the standard conditions during the physical exercise and acquiring the gait measurement data within a time interval during which the standard conditions are met.

11. The method of claim 10, further comprising testing, in the apparatus, the physiological state as a background process, wherein the testing occurs autonomously in the apparatus in an absence of a user input.

12. The method of claim 8, wherein said determining the standard conditions in the apparatus comprises:
detecting, after the physical exercise, on a presence of the standard conditions from measurement data acquired during the physical exercise;
extracting from the gait measurement data acquired during the physical exercise measurement data measured when the standard conditions are met; and
determining the physiological state from the extracted measurement data as a post-processing after the physical exercise.

13. The method of claim 8, further comprising using, in the apparatus, heart activity data measured during the physical exercise by a heart activity sensor as a reference for determining on a presence of the standard conditions.

14. The method of claim 8, further comprising using, in the apparatus, at least one of step interval variability and stride interval variability measured during the physical exercise as a reference for determining on a presence of the standard conditions.

15. The method of claim 8, further comprising:
determining, in the apparatus, a difference between the standard conditions and conditions prevailing during the exercise;
determining, in the apparatus, a scaling factor for the gait measurement data; and
scaling, in the apparatus, the gait measurement data with the scaling factor to provide the standard conditions.

16. An apparatus comprising:
at least one processor; and
at least one memory including a computer program, wherein the at least one memory and the computer program-are configured, with the at least one processor, to cause the apparatus to perform operations comprising:
acquiring gait measurement data from at least one motion sensor representing measured gait of a user during a physical exercise;
computing at least one of step interval variability and stride interval variability from the gait measurement data;
determining, in the apparatus, standard conditions for testing a level of fatigue;
determining, by the apparatus, the user's level of fatigue from said at least one of step interval variability and stride interval variability and using, in the determination of the level of fatigue, exclusively gait measurement data measured under the standard conditions by excluding from the determination of the level of fatigue the gait measurement data that has been measured outside the standard conditions; and
determining when the standard conditions are satisfied by using the following steps (a) and (b):
(a) the standard conditions are defined by heart activity measurement data received from a heart activity sensor and at least one threshold or range for the heart activity measurement data, and the apparatus compares the measured heart activity measurement data with the at least one thresh-old or range; if the heart activity measurement data falls outside the range defining the standard conditions, the apparatus determines the standard conditions not to have been met; and
if the heart activity measurement data falls within the range defining the standard conditions, the apparatus determines the standard conditions to have been met;
(b) the standard conditions are defined by running speed measured from the gait measurement data during the exercise with prior knowledge of a step length or a stride length; if the measured running speed falls within a predetermined range de-fining the standard conditions, the apparatus determines the standard conditions to be fulfilled; and if the measured running speed falls outside the predetermined range defining the standard conditions, the apparatus determines the standard conditions not to be fulfilled.

17. The apparatus of claim 16, wherein the at least one memory and the computer program are configured, with the at least one processor, to cause the apparatus to perform operations comprising determining the physiological state to be inversely proportional to the step interval variability and stride interval variability such that a higher step interval variability and a higher stride interval variability is associated with a poorer physiological state.

18. The apparatus of claim 16, wherein the at least one memory and the computer program are configured, with the at least one processor, to cause the apparatus to perform operations comprising determining the user's physiological state by comparing said at least one of step interval variability and stride interval variability with at least one predetermined threshold.

19. The apparatus of claim 16, wherein the at least one memory and the computer program are configured, with the at least one processor, to cause the apparatus to perform operations comprising:
determining standard conditions for testing the physiological state; and
using in the determination of the physiological state exclusively gait measurement data measured under the determined standard conditions.

20. A computer program product embodied on a non-transitory distribution medium readable by a computer and comprising program instructions which, when executed by the computer, performs a computer process comprising:
- acquiring gait measurement data representing measured gait of the user from at least one motion sensor during a physical exercise;
- computing at least one of step interval variability and stride interval variability from the gait measurement data;
- determining, in the apparatus, standard conditions for testing a level of fatigue;
- determining, by the apparatus, the user's level of fatigue from said at least one of step interval variability and stride interval variability and using, in the determination of the level of fatigue, exclusively gait measurement data measured under the standard conditions by excluding from the determination of the level of fatigue the gait measurement data that has been measured outside the standard conditions; and
- determining when the standard conditions are satisfied by using the following steps (a) and (b):
  - (a) the standard conditions are defined by heart activity measurement data received from a heart activity sensor and at least one threshold or range for the heart activity measurement data, and the apparatus compares the measured heart activity measurement data with the at least one threshold or range; if the heart activity measurement data falls outside the range defining the standard conditions, the apparatus determines the standard conditions not to have been met; and if the heart activity measurement data falls within the range defining the standard conditions, the apparatus determines the standard conditions to have been met;
  - (b) the standard conditions are defined by running speed measured from the gait measurement data during the exercise with prior knowledge of a step length or a stride length; if the measured running speed falls within a predetermined range de-fining the standard conditions, the apparatus determines the standard conditions to be fulfilled; and if the measured running speed falls outside the predetermined range defining the standard conditions, the apparatus determines the standard conditions not to be fulfilled.

* * * * *